(12) United States Patent
Jung et al.

(10) Patent No.: US 10,905,655 B2
(45) Date of Patent: Feb. 2, 2021

(54) COMPOSITION FOR PREVENTING OR TREATING STENOSIS INCLUDING BROWN ALGAE EXTRACT

(71) Applicant: PUKYONG NATIONAL UNIVERSITY INDUSTRY-UNIVERSITY COOPERATION FOUNDATION, Busan (KR)

(72) Inventors: Won-Kyo Jung, Busan (KR); Seok-Chun Ko, Jeju-si (KR); Min-Seon Jeong, Busan (KR); Hyoung-Shin Lee, Busan (KR); Sung-Won Kim, Busan (KR); Chul-Ho Ok, Busan (KR); JungHwan Oh, Busan (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 15/738,933

(22) PCT Filed: Nov. 20, 2017

(86) PCT No.: PCT/KR2017/013195
§ 371 (c)(1),
(2) Date: Dec. 21, 2017

(87) PCT Pub. No.: WO2018/128263
PCT Pub. Date: Jul. 12, 2018

(65) Prior Publication Data
US 2019/0380975 A1 Dec. 19, 2019

(30) Foreign Application Priority Data
Jan. 5, 2017 (KR) ........................ 10-2017-0001752

(51) Int. Cl.
| | | |
|---|---|---|
| A61K 36/00 | (2006.01) |
| A61K 31/05 | (2006.01) |
| A61P 11/04 | (2006.01) |
| A61K 36/03 | (2006.01) |
| A61K 47/34 | (2017.01) |
| A61L 29/08 | (2006.01) |
| A61L 29/16 | (2006.01) |

(52) U.S. Cl.
CPC .............. *A61K 31/05* (2013.01); *A61K 36/03* (2013.01); *A61K 47/34* (2013.01); *A61L 29/085* (2013.01); *A61L 29/16* (2013.01); *A61P 11/04* (2018.01); *A61L 2300/30* (2013.01)

(58) Field of Classification Search
CPC ....................................................... A61K 36/00
USPC ......................................................... 424/725
See application file for complete search history.

(56) References Cited

U.S. PATENT DOCUMENTS

2004/0170645 A1   9/2004   Daniels

FOREIGN PATENT DOCUMENTS

| KR | 10-2011-0108751 | 10/2011 |
| KR | 1020110111424 | 10/2011 |

OTHER PUBLICATIONS

Shin, Hyeon-Cheol, "Nutraceutical Application of Seanol," Food Industry and Nutrition 16, No. 1 (2011): 5-11.
Deux et al., "Low Molecular Weight Fucoidan Prevents Neointimal Hyperplasia in Rabbit Iliac Artery In-Stent Restenosis," Arteriosclerosis, Thrombosis, and Vascular Biology 22, (2002): 1604-1609.
Kim et al., "Effects of Ecklonia cava ethanolic extracts on airway hyperresponsiveness and inflammation in a murine asthma model: Role of suppressor of cytokine signaling," Biomedicine and Pharmacology 62, (2008) 289-296.
The Haerang, "To Prevent Airway Stenosis in Seaweed Extracts," Blog Naver, Dec. 20, 2017 (10:46 a.m), http://blog.naver.com/PostView.nhn?blogId=koreamof&logNo=220885835780.
"PC-Ecklonia Cava Extract" http://klinghardtacademy.com/images/stories/PC_Ecklonia_Cava/PCEckloniaCava, Aug. 10, 2016, 42 pages.
Yokogawa et al., "Inhibitory Effects of Ecklonia cava Extract on High Glucose-Induced Hepatic Stellate Cell Activation", Mar. Drugs 2011, 9, 2793-2808; doi:10.3390/md9122793; www.mdpi.com/journal/marinedrugs, 16 pages.
Korean Office Action and English Translation issued for Korean Divisional Application No. 10-2018-0018476 dated Mar. 8, 2018, 11 pages.

*Primary Examiner* — Michael V Meller
(74) *Attorney, Agent, or Firm* — Nixon & Vanderhye P.C.

(57) ABSTRACT

The present invention relates to a composition for preventing or treating stenosis, in which the composition includes brown algae extract, and more particularly to a composition for preventing or treating stenosis, in which the composition includes brown algae-derived polyphenol as an active ingredient, thereby providing excellent prevention or treatment effect on stenosis including tracheal stenosis, glottic stenosis, vascular stenosis, and the like.

1 Claim, 4 Drawing Sheets

[FIG. 1]
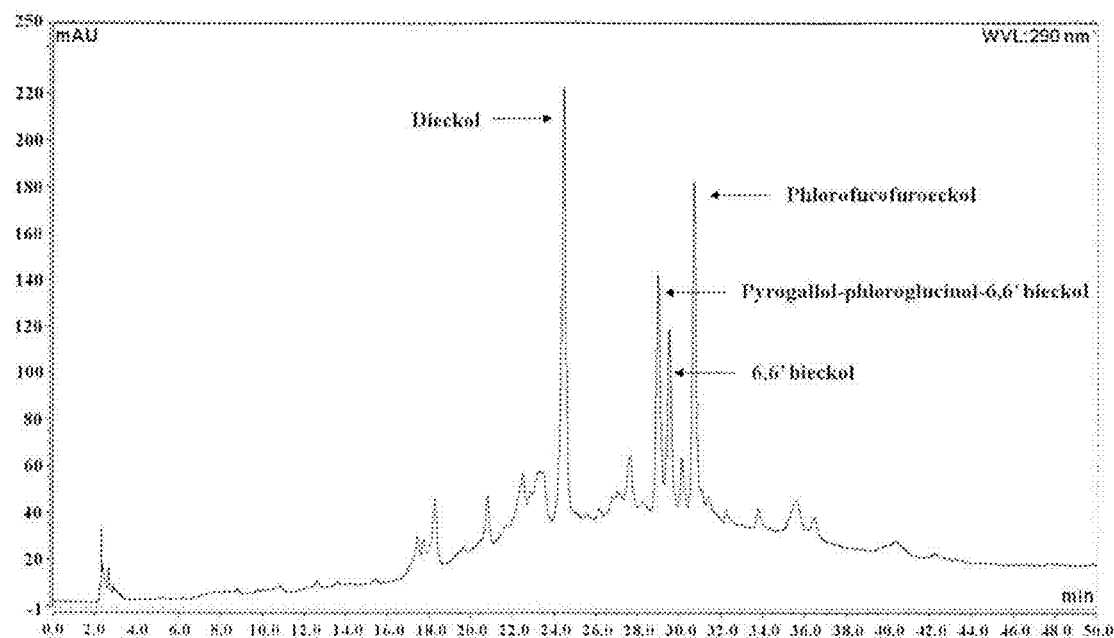
[FIG. 2]
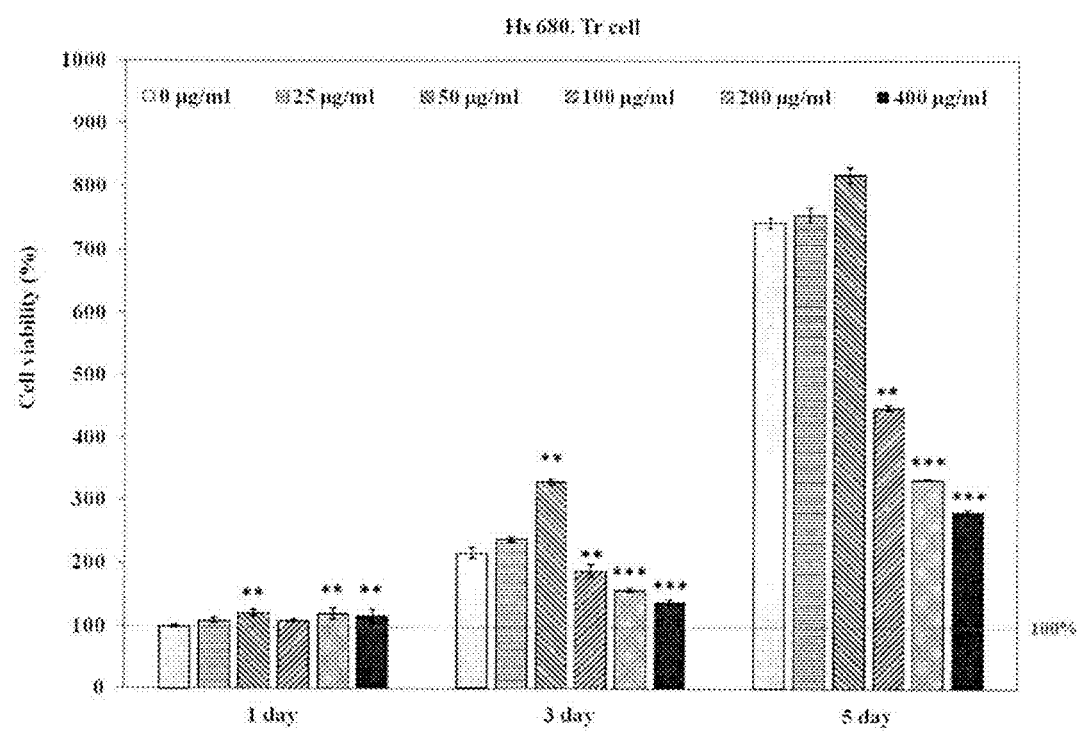

[FIG. 3]
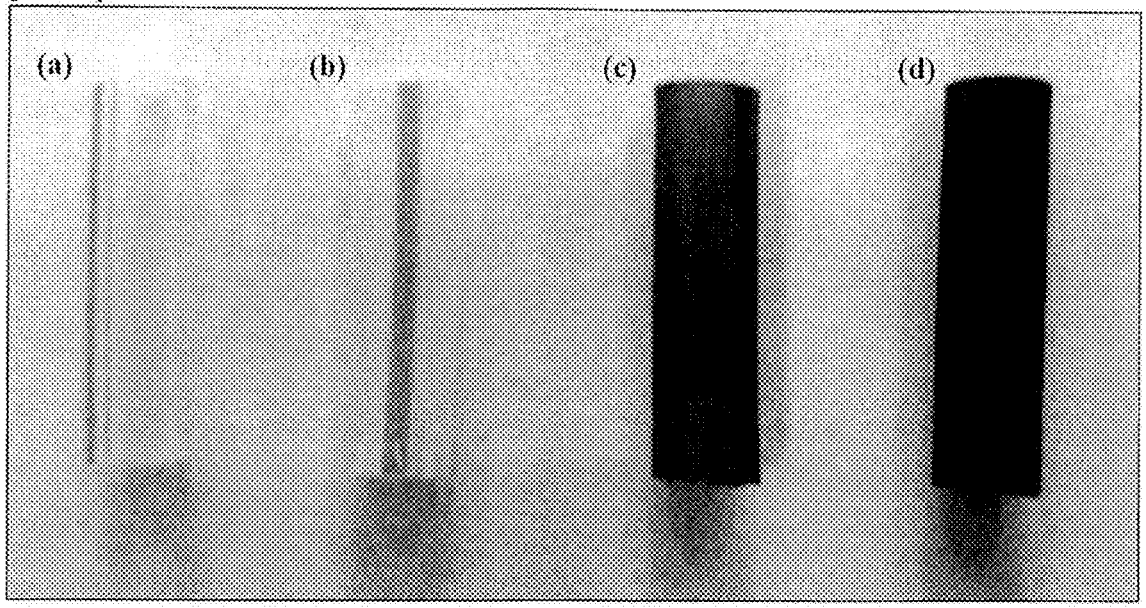
[FIG. 4]
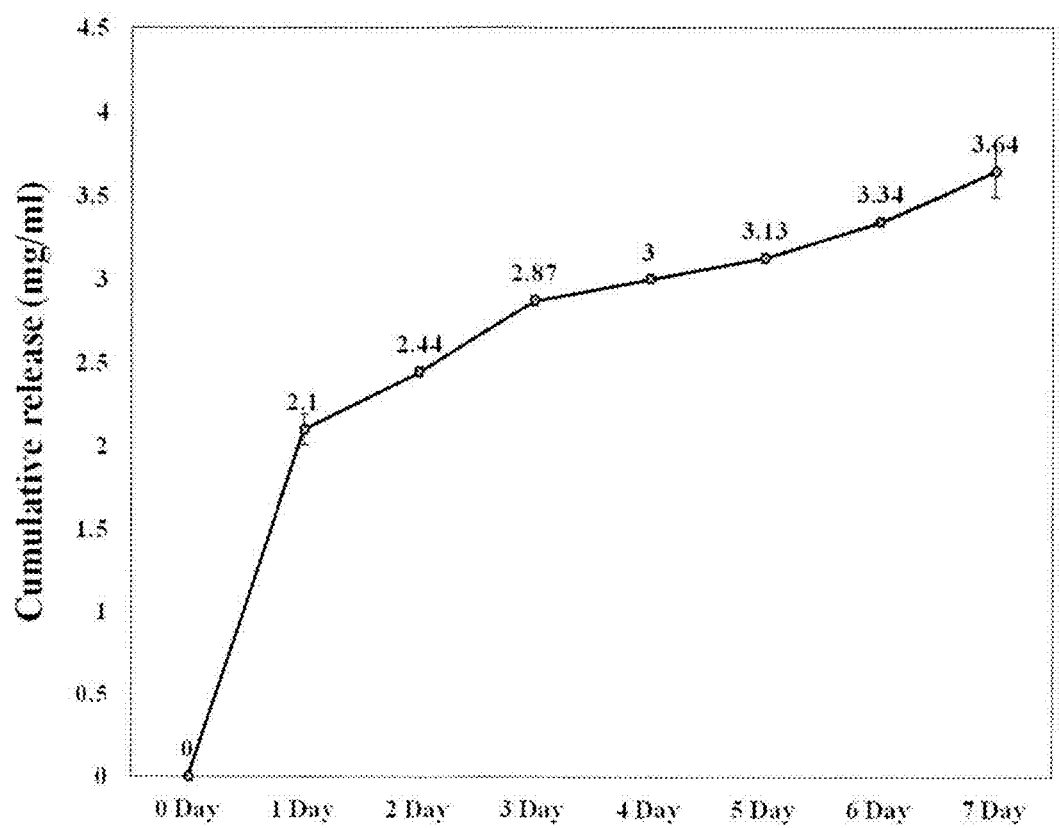

[FIG. 5]
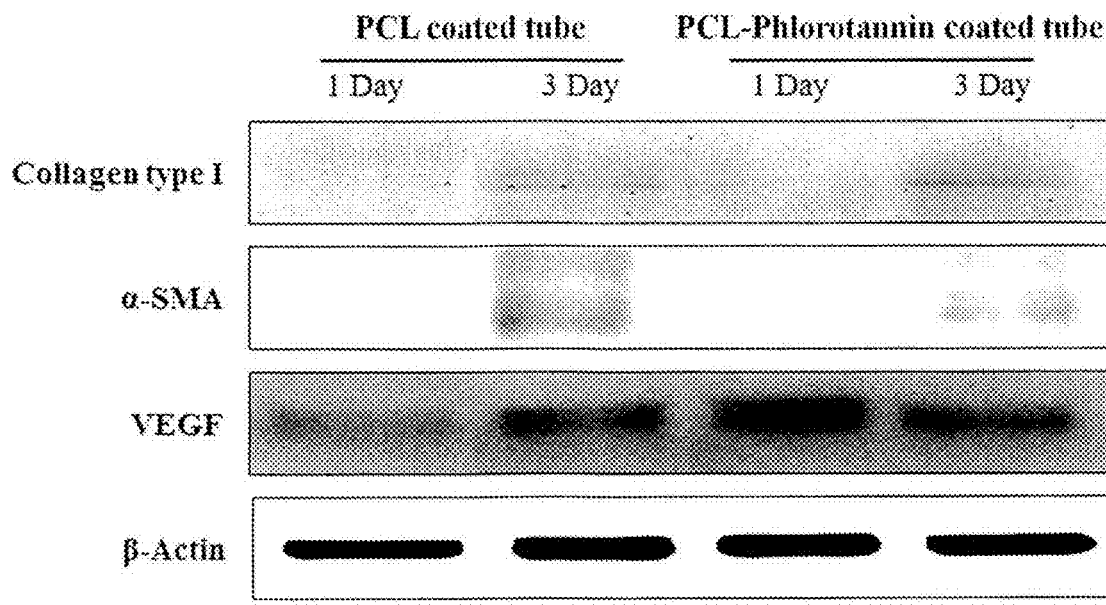
[FIG. 6]
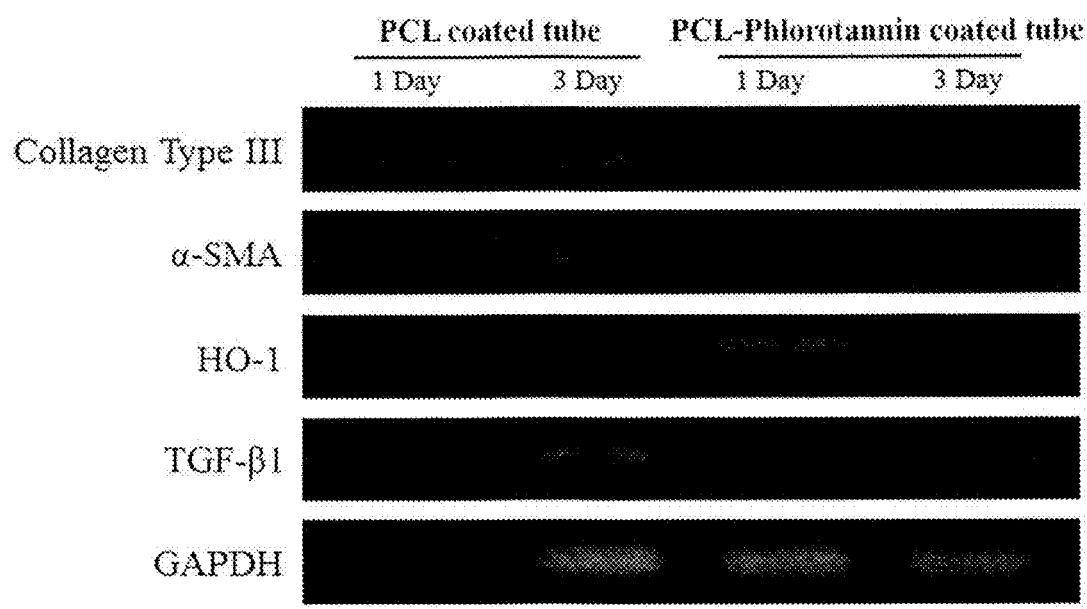

[FIG. 7]
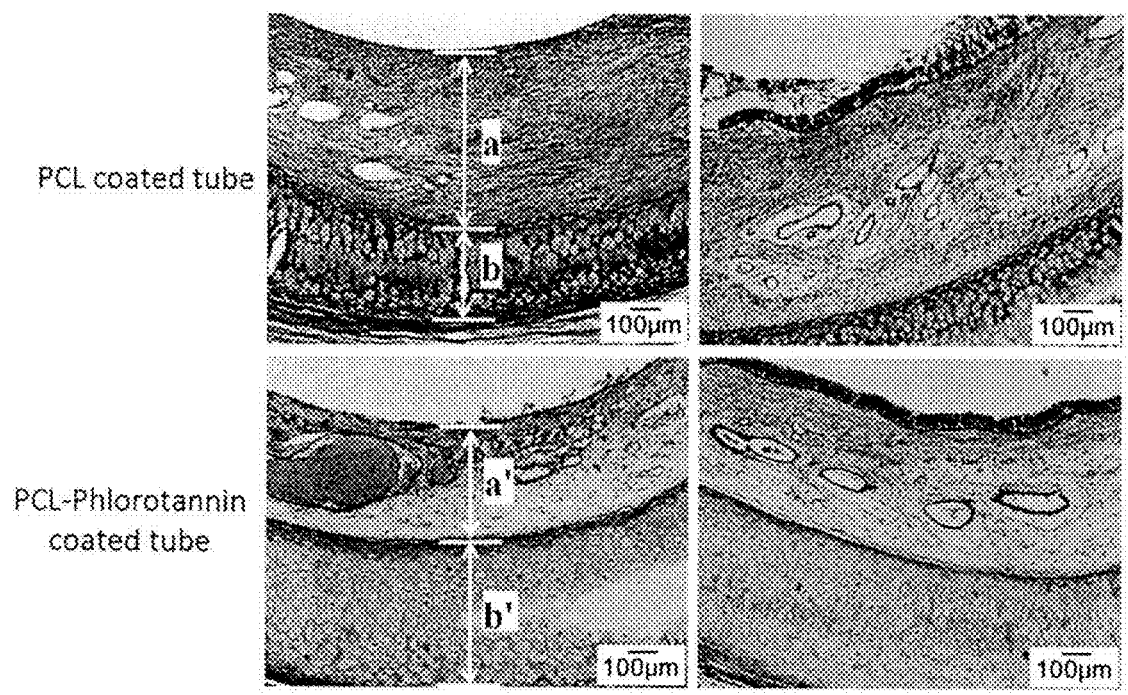

COMPOSITION FOR PREVENTING OR TREATING STENOSIS INCLUDING BROWN ALGAE EXTRACT

TECHNICAL FIELD

The present invention relates to a composition for preventing or treating stenosis, in which the composition includes brown algae extract as an active ingredient.

BACKGROUND ART

Stenosis is a disease that occurs in various organs of the body, such as tracheal stenosis, vocal stenosis, vascular stenosis, spinal stenosis, and pyloric stenosis.

The tracheal stenosis refers to a state in which an organ is completely or incompletely obstructed, with either congenital or acquired factor. The congenital tracheal stenosis is rare and acquired tracheal stenosis after tracheal intubation occurs most commonly. The acquired tracheal stenosis is most commonly caused by damage due to compression of the cuff of the intubation tube and damage to the tracheostomy site. In the organ tissue, inflammatory granulation tissue grows, or cicatricial contracture occurs during natural healing process due to stimulation applied during intubation and thus resulting in tracheal stenosis. It is known that trauma of the neck and long-term tracheal intubation is also the most common cause for the acquired occurrence of glottic stenosis (subglottic stenosis).

Treatment for tracheal stenosis depends on the length of the lesion site. The most common method is the resection of the lesion site and the end to end anastomosis. However, if the length of the lesion is too long to be resected, a conservative therapy that allows ventilation can be performed by a method for expanding a site corresponding to the stenosis or by a method for inserting the tube down the stenosis.

In the case of vascular stenosis, stenting is carried out on the narrowed blood vessel area. In the course of insertion of the stent into the blood vessel, the blood vessel wall is finely wounded. At this time, during natural healing, re-stenosis may occur because the inner wall tissue of the blood vessel at the wound area grows excessively and thus the vessel becomes narrow again. Most of the vascular restenosis can be treated with balloon angioplasty, other intimal resection, or installation of another stent in a stent.

Korean Patent Publication No. 2011-0111424 as a prior art disclosure discloses a system for dilating the airway stenosis region. The catheter is designed to be provided with a core having stiffness greater than that of the shaft so that the catheter is easily advanced to the constricted portion of the airway. However, this method has a problem in that airway damage may occur when the catheter is inserted.

DISCLOSURE

Technical Problem

An object of the present invention is to provide a composition for preventing or treating stenosis, in which the composition includes brown algae extract as an active ingredient.

Another object of the present invention is to provide a body intubation tube, coated with the composition as described above.

Still another object of the present invention is to provide a method for treating stenosis or complications thereof using the composition as described above.

Yet another object of the present invention is to provide a method for treating stenosis or complications thereof using a body intubation tube, coated with the composition as described above.

Technical Solution

In order to achieve the above objects, the present invention provides a composition for preventing or treating stenosis such as tracheal stenosis and glottic stenosis, in which the composition includes brown algae extract as an active ingredient.

Further, the present invention provides a body intubation tube, coated with the composition as described above.

Moreover, the present invention provides a method for treating stenosis or complications thereof, in which the method includes administering the composition in a therapeutically effective amount to a patient in need of treatment of stenosis or complications thereof.

Furthermore, the present invention provides a method for treating stenosis or complications thereof, in which the method includes intubating a body intubation tube, coated with the composition in the body of a patient in need of treatment of stenosis or complications thereof.

Advantageous Effects

Since the composition including the brown algae extract according to the present invention has an effect of preventing or treating stenosis, and a substance obtained from natural resources is used as an active ingredient, side effects are unlikely to be caused so that the safety can be ensured, and it can be applied to pharmaceutical compositions, medical devices, and the like.

DESCRIPTION OF DRAWINGS

FIG. 1 illustrates the results of chromatogram of *Ecklonia cava* extract by high-performance liquid chromatography.

FIG. 2 illustrates the results of measuring the proliferation inhibitory effect of human-derived airway fibroblasts on *Ecklonia cava* extract.

FIG. 3 illustrates the appearance of tracheal intubation tubes coated with *Ecklonia cava* extract.

FIG. 4 illustrates the results of measuring the amount of polyphenol released from a 10% PCL twice-coated and 5% *Ecklonia cava* extract-coated tube.

FIG. 5 illustrates the results of a comparison of the effect of inhibiting fibrosis on the protein expression level of the tracheal stenosis animal models in which 10% PCL-coated tube and 10% PCL twice-coated and 5% *Ecklonia cava* extract-coated tube are intubated.

FIG. 6 illustrates the results of a comparison of the effect of inhibiting fibrosis on mRNA expression levels of the tracheal stenosis animal models in which 10% PCL-coated tube and 10% PCL twice-coated and 5% *Ecklonia cava* extract-coated tube are intubated.

FIG. 7 illustrates the results of a comparison of collagen accumulation in the tracheal stenosis animal models in which 10% PCL-coated tube and 10% PCL twice-coated and 5% *Ecklonia cava* extract-coated tube are intubated.

BEST MODE

Hereinafter, exemplary embodiments of the present invention will be described in detail. However, these are merely examples, and the present invention is not limited thereto.

The present invention provides a composition for preventing or treating stenosis, in which the composition includes brown algae extract as an active ingredient.

In the present invention, stenosis is acquired and may be one that occurs in the course of natural healing due to external damage applied to the tissue. Stenosis that may be caused by external injury includes tracheal stenosis, glottic stenosis, and vascular restenosis after stenting. Preferably, the stenosis may be tracheal stenosis or glottic stenosis.

In the present invention, the brown algae refer to one group of protist organisms belonging to marine and multicellular algae. The brown algae may be sea mustard, kelp, gulfweed, seaweed fusiforme, sea trumpet (*Ecklonia cava*), and the like, and may preferably be *Ecklonia cava*.

In an embodiment of the present invention, the brown algae extract may be prepared using hot water extraction, distillation extraction, solvent extraction, ultrasonic extraction, supercritical extraction, or the like. An example of a method for preparing the brown algae extract is described in detail as follows. After washing the brown algae, they are pulverized and powdered. The powdered brown algae are extracted with a solvent to obtain the brown algae extract. In the process of powdering the brown algae, the washed brown algae may be freeze-dried and then pulverized to powder. A step of volatilizing the solvent included in the brown algae extract may further be included. The solvent included in the brown algae extract is volatilized and then is freeze-dried to obtain extract powders. Then the extract powders are dissolved in a solvent to prepare the brown algae extract.

The brown algae extract may be extracted with alcohol. The alcohol may be a low order alcohol, preferably ethanol.

In one embodiment of the present invention, the brown algae extract may include brown algae-derived polyphenol. The polyphenol in the present invention refers to a molecule in which two or more hydrogen atoms of benzene are substituted with hydroxy groups. Specifically, the polyphenol may be a kind of flavonoid, a kind of phlorotannin, or the like.

In one embodiment of the present invention, the concentration of polyphenol in the brown algae extract may be at least 2% by weight, preferably at least 5% by weight, based on solids. Below the range, as described above, the effect of inhibiting stenosis may not be exhibited. In the present invention, the upper limit of the content of the brown algae-derived polyphenol is not particularly limited, but if considering that the effect of addition increases no longer, the upper limit may be, for example, 80% by weight, but is not limited thereto. The concentration of polyphenol in the brown algae extract may be controlled by adjusting the amount of extraction solvent used, time, and the like.

In one embodiment of the present invention, the brown algae-derived polyphenol may be, for example, phlorotannin.

In the present invention, the phlorotannin refers to an oligomer composed of phloroglucinol as a monomer. Preferably, the phlorotannin may be eckol, dieckol, 6,6'-bieckol, 8,8'-bieckol, 2-O-(2,4,6-trihydroxyphenyl)-6,6'-bieckol, eckstolonol, fucofuroeckol, phlorofucofuroeckol, 2-phloroeckol, 3-phloroeckol, 7-phloroeckol, diphlorethol, triphlorethol A, phlorotannin A, pyrogallol-phloroglucinol-6,6'-bieckol, phloroglucinol, and the like. More preferably, the phlorotannin may be eckol, dieckol, 6,6'-bieckol, eckstolonol, phlorofucofuroeckol, triphlorethol A, and pyrogallol-phloroglucinol-6,6'-bieckol.

The present invention provides a body intubation tube, coated with a composition including the brown algae extract. The brown algae may be sea mustard, kelp, gulfweed, seaweed fusiforme, sea trumpet (*Ecklonia cava*), and the like, and may preferably be *Ecklonia cava*.

In one embodiment of the present invention, the brown algae extract may include the brown algae-derived polyphenol, and the brown algae-derived polyphenol may be phlorotannin.

In one embodiment of the present invention, a composition including the brown algae extract may be applied to a medicament or a medical device for preventing or treating stenosis. Preferably the composition is applied to a body intubation tube. For example, tracheal stenosis or glottic stenosis may often be caused by side effects after tube intubation. In one embodiment of the present invention, the body may be one of an object having an organ to which an intubation tube may be applied. Preferably, it may be a human or animal body.

An example of a method for coating the composition including brown algae extract on a body intubation tube is as follows. The method may include (a) preparing a tube, (b) coating the tube with a composition including brown algae extract, (c) washing the coated tube, and (d) drying the washed tube.

In one embodiment of the present invention, a coating layer of a composition including brown algae extract may be formed on a polycaprolactone (PCL) coating layer. The PCL coating layer may provide the effect of controlling the release of polyphenol, an ingredient contained in the brown algae extract. Accordingly, the method may further include coating a PCL solution prior to the coating the composition including the brown algae extract on the tube. For example, the method may include (a) preparing a tube, (b) coating the tube with a PCL solution, (c) coating the dried tube with a composition including brown algae extract, (d) washing the PCL and brown algae extract-coated tube, and (d) drying the washed tube. More preferably, the step of (b) may be repeated to form a plurality of PCL coating layers. If necessary, the method may further include drying the PCL solution-coated tube after the step of (b).

Examples of the method of coating a body intubation tube with the composition including the brown algae extract include solution coating, film coating, electrospinning, and three-dimensional printing, and the like.

The present invention provides a method for treating stenosis or complications thereof, in which the method includes administering the composition including the brown algae extract in a therapeutically effective amount to a patient in need of treatment of stenosis or complications thereof.

Here, the stenosis may include, for example, tracheal stenosis or glottic stenosis, and may be caused by side effects after tube intubation.

The present invention provides a method for treating stenosis or complications thereof, in which the method includes intubating a brown algae extract-coated body intubation tube into the body of a patient in need of treatment of stenosis or complications thereof.

Here, the stenosis may include, for example, tracheal stenosis or glottic stenosis, and may be caused by side effects after tube intubation.

As used herein, the term "prevention" refers to any action that inhibits or delays the onset by the administration of the composition. In the present invention, the term "treatment" means any action that improves or benefits the symptoms of the disease by administration of the composition.

In the present invention, "administration" refers to providing a predetermined substance to a patient in any suitable manner, and the composition of the present invention may be orally or parenterally administered through any common route in which the composition may arrive at the target tissue. Further, the composition may be applied to any device or medical device in which an active ingredient can move to the target cell and thus may be administered. Preferably, the composition is applied to a body intubation tube. When a body intubation tube coated with the composition is intubated to a patient, the active ingredient of the composition may be released into the body, thereby exhibiting the preventive and therapeutic effect.

When the composition for preventing or treating stenosis according to the present invention is formulated, it is prepared using a diluent or an excipient such as a filler, an extender, binders, a wetting agent, a disintegrant, a surfactant, and the like, which is commonly used.

A solid formulation for oral administration includes a tablet, a pill, powder, a granule, a capsule, a troche, and the like. Solid formulations may be prepared by mixing the composition of the present invention with at least one excipient such as starch, calcium carbonate, sucrose, lactose, gelatin, or the like. Further, a lubricant such as magnesium stearate talc is used in addition to a simple excipient. A liquid preparation for oral administration includes a suspension, a solution, an emulsion, syrups, or so on. In addition to a commonly used diluent such as water and liquid paraffin, various excipients such as a wetting agent, a sweetening agent, a fragrance, a preservative, and the like can be included.

A formulation for parenteral administration includes a sterilized aqueous solution, a non-aqueous solution, a suspension, an emulsion, a freeze-dried preparation, a suppository, and the like.

Propylene glycol, polyethylene glycol, vegetable oil such as olive oil, an injectable ester such as ethyl oleate, and the like are used as a non-aqueous solvent and suspending agent. Witepsol, macrogol, tween 61, cacao paper, laurin, glycerol, gelatin, and the like may be used as a base for the suppository.

The composition according to the present invention is administered in a pharmaceutically effective amount. In the present invention, "pharmaceutically effective amount" means an amount sufficient to treat a disease at a reasonable benefit/risk ratio applicable to medical treatment. The effective dose level may be determined depending on factors such as the type of disease, severity, activation of the drug, sensitivity to the drug, administration time, administration route, excretion rate, treatment duration, co-administered drugs, and other factors well known in the medical arts. The composition of the present invention may be administered as an individual therapeutic agent or in combination with other therapeutic agents. The composition may be administered sequentially or concurrently with conventional therapeutic agents. The composition may be administered singly or multiply. By considering all of the above factors, the composition is administered in the amount in which the maximum effect can be obtained in a minimal amount of the composition without side effects, which is important and can be easily determined by those skilled in the art.

In particular, the effective amount of the composition according to the present invention may vary depending on the age, sex, and body weight of a patient. In general, 0.1 mg to 100 mg, preferably 0.5 mg to 10 mg per 1 kg of body weight may be administered daily or every other day or one time to three times a day. However, the dosage may be varied depending on the route of administration, the severity of obesity, sex, weight, age, and the like so that the scope of the present invention is not limited to the dosage by any means.

MODE OF THE INVENTION

Hereinafter, preferred embodiments of the present invention will be described for an understanding of the present invention, but these embodiments are illustrative of the present invention and are not intended to limit the scope of the appended claims. It will be apparent to those skilled in the art that various changes and modifications can be made to the embodiments within the scope and spirit of the present invention, and such variations and modifications are within the scope of the appended claims.

Example 1. Preparation of *Ecklonia cava* Extract

Brown algae (*Ecklonia cava*) were collected from Jeju Island. The collected *Ecklonia cava* was washed three times with running water to remove salinity, epiphyte, sand, and so forth positioned on the surface. Then it was carefully washed in clean water and stored at −80° C. The frozen *Ecklonia cava* was lyophilized and then finely ground. The powdery *Ecklonia cava* was extracted three times with 4 L of 70% ethyl alcohol (ethanol), and the residue was removed by decompression filtration. Then the alcohol was volatilized using a vacuum concentrator at 40° C., and then the extract powder was obtained through freeze-drying. The extract powder was dissolved in ethanol to obtain *Ecklonia cava* extract.

Experimental Example 1. Measurement of Polyphenol and Other Component Content of *Ecklonia cava* Extract The polyphenol content of the *Ecklonia cava* extract obtained in Example 1 was measured. The polyphenol content was measured in accordance with means used by Shetty et al. 1 mL of a 95% ethanol solution and 5 mL of distilled water were added to 1 mL of the extract and they were mixed. Then 0.5 mL of 50% Folin-Ciocalteu reagent (Sigma Chemical, St. Louis, Mo.) was added thereto, followed by reaction for five minutes. 1 mL of 5% sodium carbonate ($Na_2CO_3$) solution was added thereto, followed by reaction for one hour in a dark state. Then the absorbance thereof was measured at 725 nm. At this time, in the standard calibration curve, the total amount of polyphenol was calculated from a standard curve prepared by the same method using gallic acid as a standard material.

Further, for another general component of the *Ecklonia cava* extract, moisture content was measured by the air-oven method at 105° C., crude fat was measured by Soxhlet extraction method, crude protein was measured by Kjeldahl method, and crude ash was measured by dry ashing method at 550° C. according to AOAC method.

The carbohydrate content was calculated by subtracting moisture, ash, crude protein, crude fat, and polyphenol contents from the total content of extracted solids (See Table 1).

TABLE 1

| moisture | crude ash | crude protein | crude fat | carbo-hydrate | poly-phenol |
|---|---|---|---|---|---|
| 6.09% | 5.12% | 4.95% | 13.66% | 24.19% | 45.99% |

High performance liquid chromatography (HPLC) analysis of *Ecklonia cava* extract was performed using a linear concentration gradient solvent system in which 20 μL of 5 mg/mL *Ecklonia cava* extract was directly injected into a $C_{18}$ reverse phase column. The mobile phase changed the ratio by methanol-water as follows. Methanol including 0.1% formic acid and water including 0.1% formic acid were flowed from 5% to 100% for 0 minute to 50 minutes at flow rate of 0.5 mL/min, and UV absorbance thereof was measured at 290 nm.

As a result, the *Ecklonia cava* extract included a large amount of polyphenol (See Table 1). It was confirmed that the polyphenol included in the *Ecklonia cava* extract was phlorotannin through HPLC results (See FIG. 1). The *Ecklonia cava* extract of Example 1 included compounds of dieckol, 6,6'-bieckol, pyrogallol-phloroglucinol-6,6'-bieckol, and phlorofucofuroeckol.

Experimental Example 2. Effect of Inhibiting Proliferation of Fibroblasts by *Ecklonia cava* Extract Hs 680. Tr human tracheal fibroblast cell, which is human-derived tracheal fibroblast, was used. The frozen cells were melted in a constant-temperature water bath at 37° C., and the medium was added thereto, followed by centrifugation at 100 g (747 rpm) for three minutes using a centrifuge. The pellet remained, and all supernatants were removed. Then they were suspended by adding a fresh medium. Subsequently, they were subcultured in 100 mm dishes.

The above-described prepared fibroblasts, respectively, were treated with the extract solution obtained by dissolving the extract powder of Example 1 in dimethylsulfoxide (DMSO) to have final concentrations of 0, 25, 50, 100, 200, and 400 μg/ml. The effect of inhibiting proliferation of cells was confirmed by MTT (3-(4,5-Dimethylthiazol-2-yl)-2,5-diphenyltetrazolium bromide) assay on the first, third, and fifth day, and the graphs of their results were illustrated in FIG. 2.

As illustrated in FIG. 2, it was confirmed that the *Ecklonia cava* extract suppresses the proliferation of fibroblasts. On the first day after the treatment with the *Ecklonia cava* extract, the cell proliferation rate was similar to that of the untreated cells regardless of the treatment concentration. From the third day after the treatment, the effect of inhibiting proliferation of fibroblasts occurred. In comparison with the proliferation rate of untreated cells, the effect of inhibiting proliferation was exhibited in fibroblasts treated with the *Ecklonia cava* extracts including 100 μg/ml, 200 μg/ml, and 400 μg/ml of polyphenol. On the fifth day after treatment with *Ecklonia cava* extract, the effect of inhibiting proliferation of fibroblasts was also observed in the fibroblasts treated with the *Ecklonia cava* extracts including 100 μg/ml, 200 μg/ml, and 400 μg/ml of polyphenol. It was confirmed that the effect of inhibiting proliferation of fibroblasts was greater at the fifth day than at the third day.

Comparative Example 1. Preparation of Intubation Tube Coated Only with PCL Solution Polycaprolactone (PCL) was dissolved in chloromethane to prepare 10% PCL solution, and then a silicon intubation tube was coated by immersing the tube in the 10% PCL solution. After PCL coating, air-drying was performed for 24 hours in Hume hood.

FIG. 3 (*a*) illustrates a tube without any coating and FIG. 3 (*b*) illustrates a tube coated with 10% PCL (Comparative Example 1, 10% PCL-coated tube).

Examples 2-3. Preparation of Intubation Tube Coated with PCL Solution and *Ecklonia cava* Extract In the same scheme as in Comparative Example 1, PCL was dissolved in chloromethane to prepare 10% PCL solution. Then, a silicon intubation tube was coated by immersing the tube in the 10% PCL solution. The PCL coating is to control the drug delivery of coated *Ecklonia cava* extract. After PCL coating, air-drying was performed for two hours in Hume hood. To perform the PCL coating twice, the tube was coated with 10% PCL solution again, and then the tube was air-dried for 24 hours in Hume hood in the same scheme.

The *Ecklonia cava* extract powder of Example 1 was dissolved in 70% ethanol to prepare 5% (w/v) *Ecklonia cava* extract. Then the tube which went through a drying process was immersed in the 5% *Ecklonia cava* extract solution and coated on the agitator for 24 hours at room temperature. After coating, the tube was lightly inverted and washed 20 times with distilled water. Such a washing process was carried out five times. The tube was air-dried for 24 hours in Hume hood and stored at 4° C. in a dark room.

FIG. 3 illustrates the appearance of PCL-*Ecklonia cava* extract coated tube (PCL and phlorotannin-coated tube). FIG. 3 (*c*) illustrates 10% PCL once-coated and 5% *Ecklonia cava* extract-coated tube (Example 2), and FIG. 3 (*d*) illustrates 10% PCL twice-coated and 5% *Ecklonia cava* extract-coated tube (Example 3).

Referring to FIGS. 3 (*c*) and (*d*), it can be confirmed that a larger amount of the *Ecklonia cava* extract is coated by twice-coating the tube with the PCL solution.

Experimental Example 3. Measurement of Amount of Polyphenol Released from Tube Coated with *Ecklonia cava* Extract In order to measure the amount of polyphenol released from Example 3 (FIG. 3 (*d*)), the tube of Example 3 was immersed in 10 mL PBS and placed at 37° C. to measure the amount of polyphenol released. After 24 hours of immersing the tube in PBS, 100 μL PBS was taken out and polyphenol assay was performed.

To prepare a standard curve, phloroglucinol at concentrations of 0, 10, 20, 50, 100, 200, 500, and 1,000 μg/ml was prepared and dispensed in a volume of 20 μL into 96-well plate. PBS samples were also dispensed in a volume of 20 μL into the 96-well plate. Then, 100 μL of 1N Folin-Ciocalteu reagent was added to the 96-well plate. They were wrapped with foil and then reacted at room temperature for three minutes. After the reaction, 80 μL of 7.5% sodium carbonate ($Na_2CO_3$) was further added. They were reacted at room temperature for 20 minutes while the light was blocked with foil. The absorbance was measured at 765 nm to determine the amount of polyphenol in the samples.

The released amount was measured by polyphenol assay every 24 hours and up to seven days in the same scheme.

FIG. 4 illustrates the results of measuring the amount of polyphenol released in Example 3 (FIG. 3 (d)).

Since airway intubation is performed to patients for up to seven days at hospitals in practice, the amount of polyphenol released was measured for up to seven days. It was observed that the polyphenol was released from the first day. The airway intubation is performed only for up to seven days, so the release of polyphenol from the initial stage after intubation is effective in preventing or treating stenosis. Further, the polyphenol was continuously released until the last seventh day, and the amount of polyphenol released gradually increased without rapidly increasing or decreasing. It was shown that sustainability of releasing polyphenol was excellent during the tube intubation.

Experimental Example 4. Preparation of Animal Model with Tracheal Stenosis

Male New Zealand white rabbits, which were 2.0 kg to 2.5 kg, were used as experimental animals, and the rabbits were irradiated with 10 W power for two seconds to induce stenosis.

Experimental Example 5. Confirmation of Effect of Inhibiting Fibrosis by Ecklonia cava Extract in a Protein Expression Level Each of the tube coated with 10% PCL of Comparative Example 1 (FIG. 3 (b)) and the tube coated with 10% PCL twice-coated and 5% Ecklonia cava extract of Example 3 (FIG. 3 (d)) was intubated in the airway of the stenosis-induced rabbit (Experimental Example 4). On the first day and the third day after intubation, rabbit airway was extracted, and the protein expression was confirmed.

Western blotting was used for confirming the protein expression. The extracted rabbit airway and lysis buffer were placed in a tissue crusher and disrupted. Then centrifugation was carried out. After centrifugation, the supernatant was transferred to a new tube, and the amount of protein of the supernatant was quantified. 25 µg of each protein was loaded on SDS-PAGE (polyacrylamide gel) and the electrophoresis was performed. Electro-transfer was then used to transfer the proteins in the gel to the membrane. Then each of primary antibodies that recognize collagen type I, α-SMA, VEGF, and β-Actin was reacted with the protein. Then each was reacted with a secondary antibody combined with horseradish peroxidase (HRP) which recognizes each primary antibody. Further, the degree of protein expression was confirmed by enhanced chemiluminescence (ECL) solution.

FIG. 5 illustrates the results of comparing the effect of inhibiting fibrosis at the protein expression level of the animal model with the tracheal stenosis in which the tube of Comparative Example 1 (PCL coated tube) and the tube of Example 3 (PCL and phlorotannin-coated tube) were intubated. The protein expression of collagen type I, α-smooth muscle actin (α-SMA), and vascular endothelial growth factor (VEGF), which are typical markers of collagen accumulation and fibrosis was compared. The collagen type I protein and α-smooth muscle actin (α-SMA) were less expressed in PCL and Ecklonia cava-coated tube than in PCL only-coated tube. Vascular endothelial growth factor (VEGF), in which the expression increases as the fibrosis occurs, was also less expressed in the PCL and Ecklonia cava-coated tube. In the case of vascular epidermal growth factor, when the PCL only-coated tube was intubated, the expression increased at the third day compared to the first day after the intubation, but when PCL and Ecklonia cava-coated tube was intubated, the expression decreased at the third day.

Experimental Example 6. Confirmation of Effect of Inhibiting Fibrosis by Ecklonia cava Extract in a mRNA Expression Level Each of the tube of Comparative Example 1 (FIG. 3 (b)) and the tube of Example 3 (FIG. 3 (d)) was intubated in the airway of the rabbits (Experimental Example 4) in which tracheal stenosis was induced. On the first day and third day after intubation, the rabbit airway was extracted, and mRNA expression was confirmed.

After extracting the rabbit airway, the extracted tissue was thoroughly disrupted with a Trizol solution using a tissue crusher. Then, chloroform was added and reacted for five minutes. Centrifugation was carried out at 13,000 rpm and 4° C. for 15 minutes. After centrifugation, the RNA layer was transferred to a new tube. Isopropanol was added thereto, mixed and reacted for 15 minutes. After centrifugation under the same condition, the supernatant was totally discarded, and 75% ethanol was added thereto, followed by additional centrifugation under the same condition. All supernatants were removed, followed by drying for 16 hours. Then mRNA was diluted with distilled water without RNase. After mRNA was converted to cDNA, mRNA expression in stenosis-induced tissues was compared using RT-PCR with cDNA.

FIG. 6 illustrates the results of comparing the effect of inhibiting fibrosis at the mRNA level of the tracheal stenosis-animal model in which the tube of Comparative Example 1 (PCL coated tube) and the tube of Example 3 (PCL and phlorotannin-coated tube) were intubated.

The mRNA expression of collagen type III, α-smooth muscle actin (α-SMA), hemeoxygenase-1 (HO-1), and transforming growth factor-β1 (TGF-β1), which are typical markers of collagen accumulation and fibrosis was compared. The mRNA of collagen type III, α-smooth muscle actin (α-SMA), and transforming growth factor-β1 (TGF-β1) were less expressed in PCL and Ecklonia cava-coated tube than in PCL only-coated tube. Hemoxidase-1 (HO-1) is known to inhibit fibrosis as an antioxidative marker. Expression of hemoxydesis-1 (HO-1) increased in PCL and Ecklonia cava-coated tube than in PCL only-coated tube.

Referring to the results of FIGS. 5 and 6, it was shown that the Ecklonia cava extract inhibits the mRNA and protein expression of fibrosis-related factors and promotes the expression of fibrosis-inhibiting factors.

Experimental Example 7. Confirmation of Effect of Inhibiting Collagen Accumulation by Ecklonia cava Extract Each of the tube of Comparative Example 1 (FIG. 3 (b)) and the tube of Example 3 (FIG. 3 (d)) was intubated in the airway of rabbits (Experimental Example 3) in which tracheal stenosis was induced. The tube was removed on seventh day after intubation, and the rabbit airway was extracted after four weeks from the tube removal. For the extracted rabbit airway, the collagen accumulated in the airway was stained using Masson's trichrome method.

FIG. 7 illustrates the results of comparing the collagen accumulation of the animal model with the tracheal stenosis in which the tube of Comparative Example 1 (PCL coated tube) and the tube of Example 3 (PCL and phlorotannin-coated tube) were intubated. In FIG. 7, a and a' refer to the connective tissue portion, b and b' refer to the cartilage part. Since collagen was also present in the cartilage, the cartilage was stained. Comparing a and a', the collagen accumulation was further inhibited in the PCL and *Ecklonia cava*-coated tube than in the PCL-coated tube.

INDUSTRIAL APPLICABILITY

Since the composition including the brown algae extract according to the present invention has an effect of preventing or treating stenosis, and a substance obtained from natural resources is used as an active ingredient, side effects are unlikely to be caused so that the safety can be ensured, and it can be applied to pharmaceutical compositions, medical devices, and the like and thus can be effectively used.

The invention claimed is:

1. A tube coated with *Ecklonia cava* extract and polycaprolactone.

* * * * *